United States Patent [19]
Fukui et al.

[11] Patent Number: 5,532,823
[45] Date of Patent: Jul. 2, 1996

[54] METHOD OF MEASURING OPTICAL CHARACTERISTICS OF LIQUID CRYSTAL CELLS, MEASUREMENT EQUIPMENT THEREFOR AND METHOD FOR MANUFACTURING LIQUID CRYSTAL DEVICES

[75] Inventors: Atsushi Fukui; Kanji Nishii, both of Osaka; Kenji Takamoto, Neyagawa; Masami Ito, Moriguchi, all of Japan

[73] Assignee: Matsushita Electric Industrial Co., Ltd., Kadoma, Japan

[21] Appl. No.: 361,546

[22] Filed: Dec. 22, 1994

Related U.S. Application Data

[63] Continuation-in-part of Ser. No. 206,677, Mar. 7, 1994, abandoned.

[30] Foreign Application Priority Data

Mar. 8, 1993 [JP] Japan ..................... 5-046314

[51] Int. Cl.⁶ ..................................... G01J 4/00
[52] U.S. Cl. ..................... 356/364; 356/367; 250/225
[58] Field of Search ..................... 356/364, 365, 356/366, 367, 368, 369; 250/225

[56] References Cited

U.S. PATENT DOCUMENTS

| | | | |
|---|---|---|---|
| 4,272,195 | 6/1981 | Kaye | 356/368 |
| 4,801,798 | 1/1989 | Lange | 356/367 |
| 4,973,163 | 11/1990 | Sakai et al. | 356/367 |
| 5,239,365 | 8/1993 | Inoue | 356/367 |
| 5,311,284 | 5/1994 | Nishino | 356/367 |
| 5,406,371 | 4/1995 | Sakai et al. | 356/364 |
| 5,434,671 | 7/1995 | Sumiyoshi et al. | 356/367 |

FOREIGN PATENT DOCUMENTS

| | | |
|---|---|---|
| 5-018860 | 1/1993 | Japan . |
| 5-018859 | 1/1993 | Japan . |

OTHER PUBLICATIONS

K. Sumiyoshi et al., "A New Method of TN Cell Gap Measurement" 29p-ZK-16, NEC Corporation Functional Devices Research Lab. (1993).

*Primary Examiner*—Hoa Q. Pham
*Attorney, Agent, or Firm*—McDermott, Will & Emery

[57] ABSTRACT

There is disclosed a method for measuring retardation $\Delta nd$ of a liquid crystal cell in which a linearly polarized light beam is impinged upon a liquid crystal cell, the liquid crystal cell is rotated in a plane perpendicular to an optical axis of a measuring optical system so that the transmission through the liquid crystal cell for the light beam having a polarization parallel to that of the incident light beam becomes maximal, the wavelength of the incident light beam is varied to detect at least one wavelength $\lambda_s$ at which the transmission has an extreme and, finally, $\Delta nd$ is calculated from $\Delta nd = \lambda_s \sqrt{m^2 - (1/4)}$ for the case of m-th minimal transmission or from $\Delta nd = \lambda_s \sqrt{m^2 + m}$ for the case of m-th maximal transmission.

11 Claims, 6 Drawing Sheets

METHOD OF MEASURING OPTICAL CHARACTERISTICS OF LIQUID CRYSTAL CELLS, MEASUREMENT EQUIPMENT THEREFOR AND METHOD FOR MANUFACTURING LIQUID CRYSTAL DEVICES

This is a Continuation-In-Part application of U.S. Ser. No. 08/206,677 filed on Mar. 7, 1994.

BACKGROUND OF THE INVENTION

1. Field of the Invention

The present invention relates in general to a method of measuring optical characteristics of liquid crystal cells and its applications for measurement equipment and manufacturing method of liquid crystal devices. Specifically it is concerned with a method of measuring with precision the retardation of the liquid crystal cells and equipment to measure it.

2. Description of the Prior Art

A conventional method for measuring the retardation of a birefringent material such as a liquid crystal is disclosed, for instance in U.S. Pat. Nos. 4,973,163 or 5,239,365.

The invention disclosed in U.S. Pat. No. 5,239,365 relates to measurement of the retardation of a material having a uniaxial birefringence property, in which a sample to be measured is inserted between a polarizer and an analyzer both having their directions of polarization fixed at a specified angle with each other, a variation in the intensity of light transmitted through the polarizer, sample and analyzer is detected while rotating the polarizer and analyzer relative to the sample, rotation angles of the polarizer and analyzer are set based on the detected variation in the intensity of light and the retardation of the sample is calculated based on the detected variation in the intensity of light and wavelengths of light emitted from a light source. This method is limited to uniaxial birefringent materials and, accordingly, is not available to measurement of retardation of a liquid crystal cell such as a twisted nematic liquid crystal.

On the other hand, the invention disclosed in U.S. Pat. No. 5,239,365 provides a method for measuring the retardation of a liquid crystal cell such as a twisted nematic liquid crystal. This method comprises steps; placing a liquid crystal cell between a polarizer and an analyzer in an arrangement wherein the polarization angle of the polarizer is tilted by 45° with respect to the orientation of the light entry surface of the liquid crystal cell and the polarization angle of the analyzer is tilted by 45° with respect to the orientation of the light output surface of the liquid crystal cell; measuring the strength of light transmitted through the analyzer and calculating retardation dΔn based on the measured light strength. This method, however, is applicable only for a liquid crystal cell having known rubbing directions and, accordingly, is impossible to measure the retardation of a liquid crystal cell having unknown rubbing directions. Further, it is impossible to measure the retardation accurately in the case that there exists a variety in the rubbing direction of a liquid crystal cell.

SUMMARY OF THE INVENTION

An essential object of the present invention is therefore to provide a measurement method of the retardation of liquid crystal which is capable of measuring Δnd of a liquid crystal cell exactly even if the twist angle and rubbing direction of the liquid crystal cell are unknown.

Another object of the present invention is to provide a measuring apparatus capable of measuring optical characteristics of the liquid crystal cell even if the twist angle and orientation of rubbing thereof are not known exactly.

A further object of the present invention is to provide a method of manufacturing liquid crystal devices each having a desirable value of Δnd.

In order to achieve these objects, according to the present invention, there is provided a method of measuring the Δnd of a liquid crystal cell having a known twist angle comprising steps of inputting a linearly polarized light beam into the liquid crystal cell, rotating the liquid crystal cell in a plane normal to the optical axis thereof so that the transmission of a liquid component of the light beam having passed through the liquid crystal cell and emerging therefrom, which has a polarization of the incident light beam, becomes maximal, scanning the wavelength of the incident light beam to detect at least one wavelength at which the transmission of the light component of the emerging light beam having the polarization parallel to the direction of polarization of the incident light beam has an extreme, and obtaining the Δnd of the liquid crystal cell based on the known twist angle and detected at least one wavelength.

According to a facet of the present invention, when the detected wavelength λ gives rise to m-th minimal transmission (m is a positive integer indicating an order of the minimal transmission), the Δnd is obtained from the following equation;

$$\Delta nd = \lambda \sqrt{m^2 - 1/4}$$

and, when the detected wavelength gives rise to m-th maximal transmission (m is a positive integer indicating an order of the maximal transmission), the Δnd is obtained from the following equation;

$$\Delta nd = \lambda \sqrt{m^2 + m} \quad ,$$

The device according to another facet of the present invention comprises a light source capable of emitting lights having a variety of wavelengths, means of separating a beam having a specific wavelength from the light beam emitted from the light source, a first polarizer the separated beam is incident on, a liquid crystal cell the emerging light beam from the first polarizer is incident on, means for rotating the liquid crystal cell in a plane normal to the optical axis thereof, a second polarizer the beam emerging from the liquid crystal cell is incident on and having its polarization axis parallel to that of the first polarizer, a photo detector which detects the emerging light beam from the second polarizer, and means of setting the direction of the liquid crystal cell using the means of rotating the liquid crystal cell so that an output of the photo detector has a maximal value.

Rotation of the liquid crystal cell in the plane normal to the optical axis so that the transmission for the light beam having the polarization parallel to the polarization of the incident light beam has a maximal value eliminates the dependence of the characteristics of transmission vs. wavelength on the direction of rubbing. Next the wavelength of the incident light beam on the liquid crystal cell is scanned and one measures a wavelength at which the transmission through the liquid crystal cell for the light beam component having the polarization parallel to that of the polarization of the incident light beam has an extreme. Then, one obtains the value of β at which the transmission T represented by the following equation has an extreme.

$$T = (\cos\gamma\cos\theta + (\theta/\gamma)\sin\gamma\sin\theta)^2 + ((\beta/\gamma)\sin\gamma)^2$$

where $$\gamma = \sqrt{(\beta^2 + \theta^2)}$$

where $\theta$ is the twist angle of the liquid crystal.

Finally the $\Delta nd$ is obtained from the equation $\Delta nd = \beta\lambda/\pi$.

The value $\beta$ is approximately constant when T has an extreme for the twist angle of liquid crystal being in the neighborhood of 90°. Using the relation between the $\Delta nd$ and the wavelength at which T has an extreme with the twist angle of liquid crystal being 90°, one can obtain $$\Delta nd = \lambda\sqrt{(m^2 - 1/4)},$$

where m=1, 2, 3, . . . ($\lambda$ represents a wavelength.) for the case of the extreme being minimum, and $$\Delta nd = \lambda\sqrt{(m^2 + m)},$$

where m=1, 2, 3, . . . ($\lambda$ represents a wavelength.) for the case of the extreme being maximum.

As is apparent from the mentioned above, the present invention employs a characteristic composition such that, upon measuring the retardation of a liquid crystal cell, extremes of the amount of light transmitted through an analyzer while varying the wavelength of light incident to a polarizer. This composition of the present invention has not been disclosed or suggested in U.S. Pat. Nos. 4,973,163 and 5,239,365 cited above as prior art.

Thus, the present invention enables to measure the retardation of a liquid crystal cell exactly irrespective of the twist angle and/or rubbing direction of a liquid crystal cell or even if their values are unknown.

BRIEF DESCRIPTION OF THE DRAWINGS

These and other objects and features of the present invention will become clear from the following description taken in conjunction with the preferred embodiments thereof with reference to the accompanying drawings throughout which like parts are designated by like reference numerals, and in which.

DETAILED DESCRIPTION OF THE PREFERRED EMBODIMENTS

An embodiment of the present invention, that is, a method of measuring optical characteristics of liquid crystal, is described with reference to the drawings. First the principle is explained.

Figure 1:
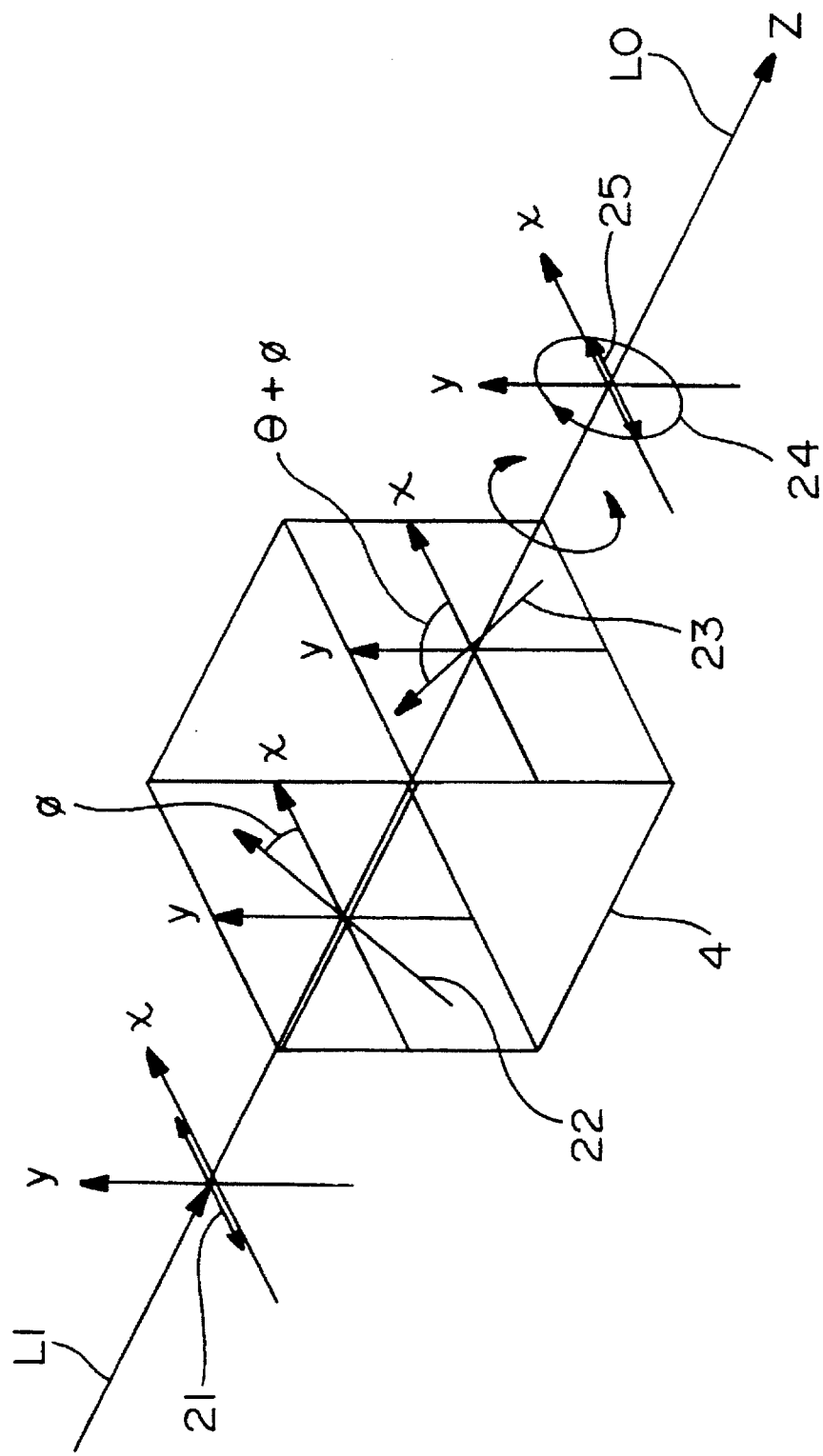
FIG. 1 is a perspective view of an essential optical system for measuring and of a liquid crystal cell according to the present invention.

FIG. 1 illustrates a light beam LI incident on and light beam LO emerging from a liquid crystal cell 4. A direction 21 of the polarization of linearly polarized incident light beam LI on liquid crystal cell 4 is set to be parallel to the x-axis, the liquid crystal being twisted by an angle $\theta$ measured counterclockwise, and a rubbing direction 22 on the incident side of liquid crystal cell 4 making angle $\phi$ measured counterclockwise with the x-axis. The retardation of liquid crystal cell 4 is $\Delta nd$.

The optical characteristics of the liquid crystal is represented by Jones matrix (1).

$$\begin{bmatrix} p + iq & r + is \\ -r + is & p - iq \end{bmatrix} \quad (1)$$

where: p1 $p = \cos\gamma\cos\theta + (\theta/\gamma)\sin\gamma\sin\theta$ $r = -\cos\gamma\sin\theta + (\theta/\gamma)\sin\gamma\cos\theta$ $q = -(\beta/\gamma)\sin\gamma\cos(\theta + 2\phi)$ $s = -(\beta/\gamma)\sin\gamma\sin(\theta + 2\phi)$ $\gamma = \sqrt{(\beta^2 + \theta^2)}$ $\beta = \pi\Delta nd/\lambda$.

Let the amplitude of linearly polarized incident light beam LI on liquid crystal cell 4 to be 1, then emerging light beam LO from liquid crystal cell 4 is given by equation (2).

$$\begin{bmatrix} p + iq & r + is \\ -r + is & p - iq \end{bmatrix} \begin{bmatrix} 1 \\ 0 \end{bmatrix} = \begin{bmatrix} p + iq \\ -r + is \end{bmatrix} \quad (2)$$

The intensity of a component of emerging light beam LO having the polarization parallel to that of incident light beam LI is given by equation (3) (note that this intensity is equal to the transmission since the amplitude of incident light beam LI is set at 1);

$$T = p^2 + q^2 = (\cos\gamma\cos\theta + (\theta/\gamma)\sin\gamma\sin\theta)^2 + ((\beta/\gamma)\sin\gamma\cos(\theta + 2\phi))^2$$

If liquid crystal cell 4 is rotated, the second term of the right hand side of equation (3) varies and T changes accordingly. Now liquid crystal cell 4 is rotated so that the transmission T becomes maximal, and T is represented by equation (4).

$$T = (\cos\gamma\cos\theta + (\theta/\gamma)\sin\gamma\sin\theta)^2 + ((\beta/\gamma)\sin\gamma)^2 \quad (4)$$

From equation (4) it follows that $$T = A\sin(2\gamma + \Gamma) + B \quad (5)$$

where $A = (1/4)\sqrt{((\cos^2(1 + (\theta/\gamma)^2) - 1)^2 + (\theta/\gamma)^2\sin^{2}2\theta)}$ $B = 1/2 + (1 - (\theta/\gamma)^2)\cos^2\theta$ $\Gamma = \tan^{-1}((-\gamma\sin^2\theta + (\theta^2/\gamma)\cos^2\theta)/(\theta\sin 2\theta))$ Since the values A, B, and $\Gamma$ vary insignificantly compared with $\sin 2\gamma$, the transmission T, therefore, changes approximately sinusoidally. Because $\gamma = \sqrt{(\beta^2 + \theta^2)}$, the transmission T also varies sinusoidally with respect to $\beta$, having maxima and minima.

Figure 2:
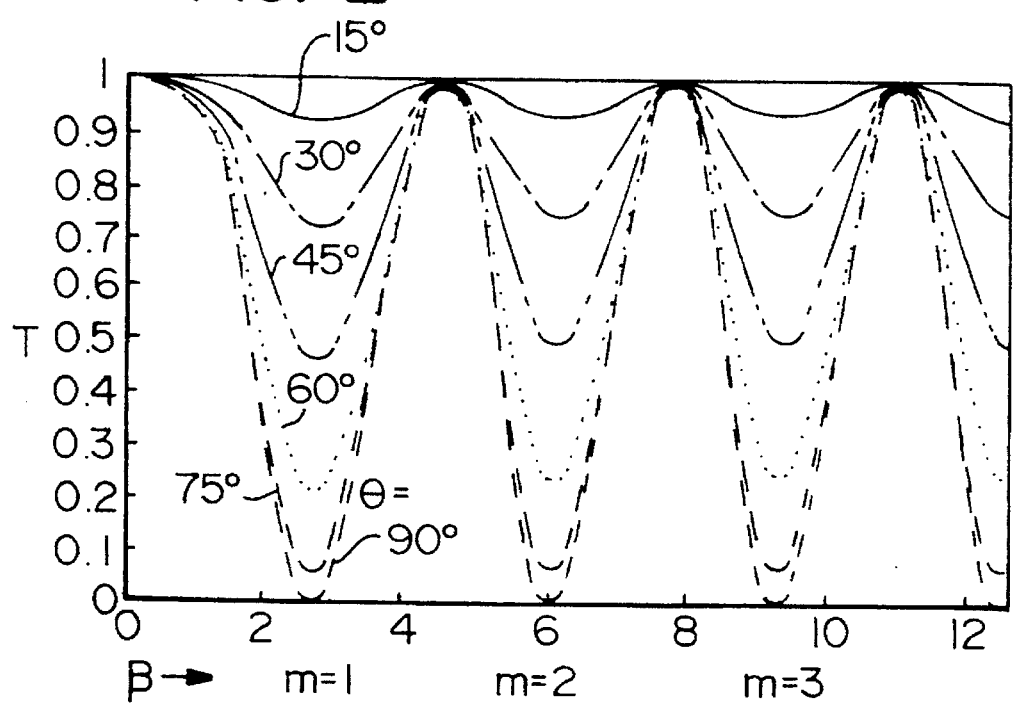
FIG. 2 is a graph showing a relationship between $\beta$ and T wherein the twist angle $\theta$ as a parameter is equal to or smaller than 90°.
Figure 3:
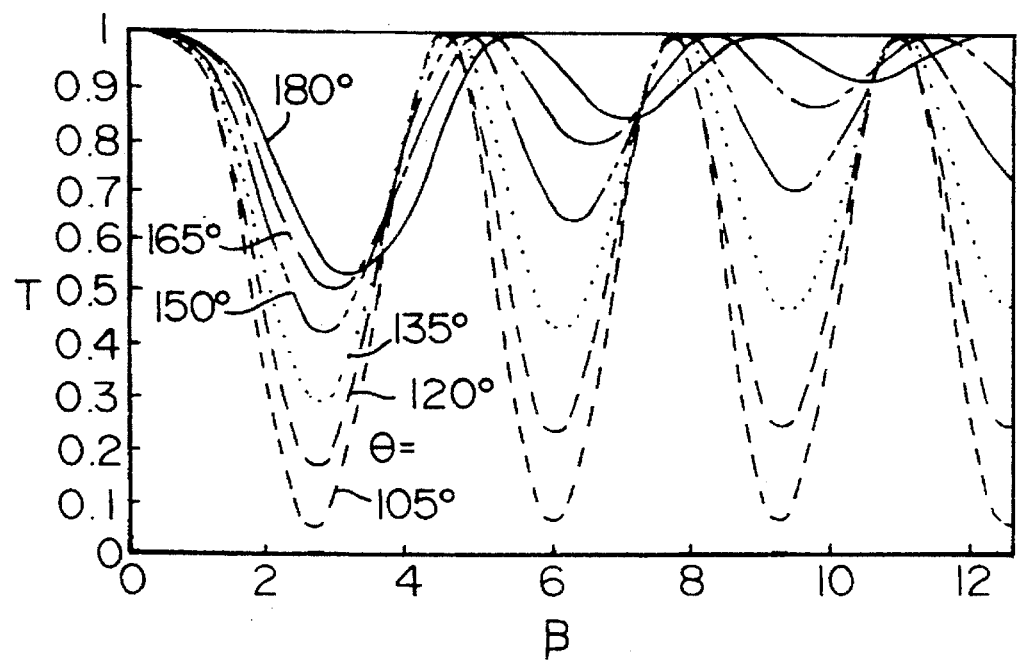
FIG. 3 is a graph showing a relationship between $\beta$ and T wherein the twist angle $\theta$ as a parameter is larger than 90°.

FIGS. 2 and 3 illustrate the relation between transmission T and $\beta$ for the twist angle $\theta$ of liquid crystal as a parameter. FIG. 2 shows the relation for $\theta$ being between 15° and 90° while FIG. 3 for $\theta$ being 105° and 180°.

Equation (4) shows that the transmission T is a function of $\beta$ and $\theta$, hence $\beta$ at which T has an extreme is a function of $\theta$. Since $\beta = \pi\Delta nd/\lambda$, the $\Delta nd$ is obtained from the wavelength $\lambda$ at which the transmission T has an extreme.

Figure 5:
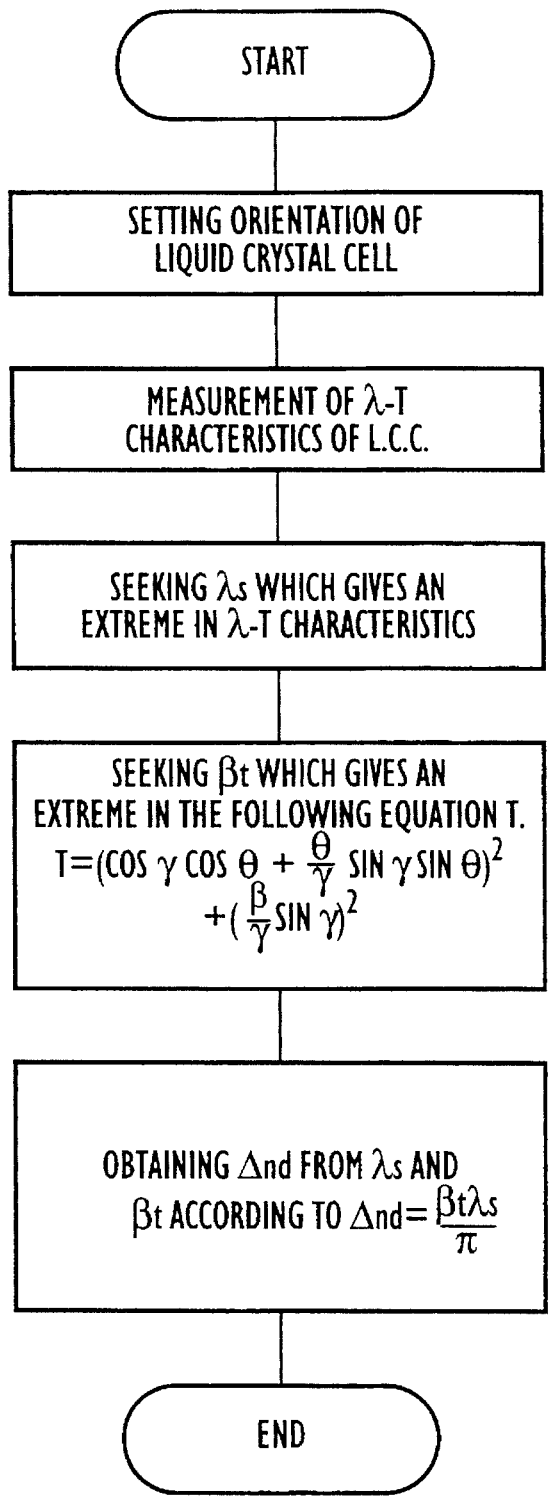
FIG. 5 is a flow chart for showing a first preferred embodiment of the measuring method of $\Delta nd$ according to the present invention.

Generally, a method of measuring optical characteristics of a liquid crystal according to the present invention is summarized in a flow chart shown in FIG. 5. That is, a linearly polarized light beam LI is incident on liquid crystal cell 4, and liquid crystal cell 4 is rotated in a plane normal to the optical axis thereof so that the transmission for a component of emerging light beam LO having a polarization parallel to that of incident light beam LI has a maximal value. In this configuration the transmission T given by equation (4) is independent of the direction of rubbing of liquid crystal cell 4. In the same configuration, the transmission is measured next in scanning the wavelength $\lambda$ of incident light beam LI and one measures the wavelengths $\lambda_s$ at which the transmission T has an extreme. Inserting the value of twist angle $\theta$ into equation (4), one obtains the values of $\beta$ (denoted as $\beta_t$) at which the transmission has an extreme. From the measured $\lambda_s$ and calculated $\beta_t$, the $\Delta nd$ of the liquid crystal cell is obtained using $\Delta nd=\beta_t\lambda_s/\pi$.

In summary, in the first embodiment of the present invention, a linearly polarized light beam is incident on the liquid crystal cell, and the liquid crystal cell is rotated in the plane normal to the optical axis so that the transmission for a component of the emerging light beam from the liquid crystal cell with the polarization parallel to that of the incident beam has a maximal value. In this configuration, the transmission T is measured in scanning the wavelength of the incident beam and the wavelengths at which the transmission has extremes are measured. The transmission in this configuration is given by $$T=(\cos \gamma \cos \theta+(\theta/\gamma) \sin \gamma \sin \theta)^2+((\beta/\gamma) \sin \gamma)^2$$

where $\gamma=\sqrt{(\beta^2+\theta^2)}$ and $\theta$ is the twist angle of the liquid crystal cell.

The values $\beta$ at which the transmission T has extremes are calculated from the above equation with the observed value of $\theta$. Finally the $\Delta nd$ of the liquid crystal cell is obtained from $\Delta nd=\beta\lambda/\pi$ independently of the direction of rubbing.

Figure 4:
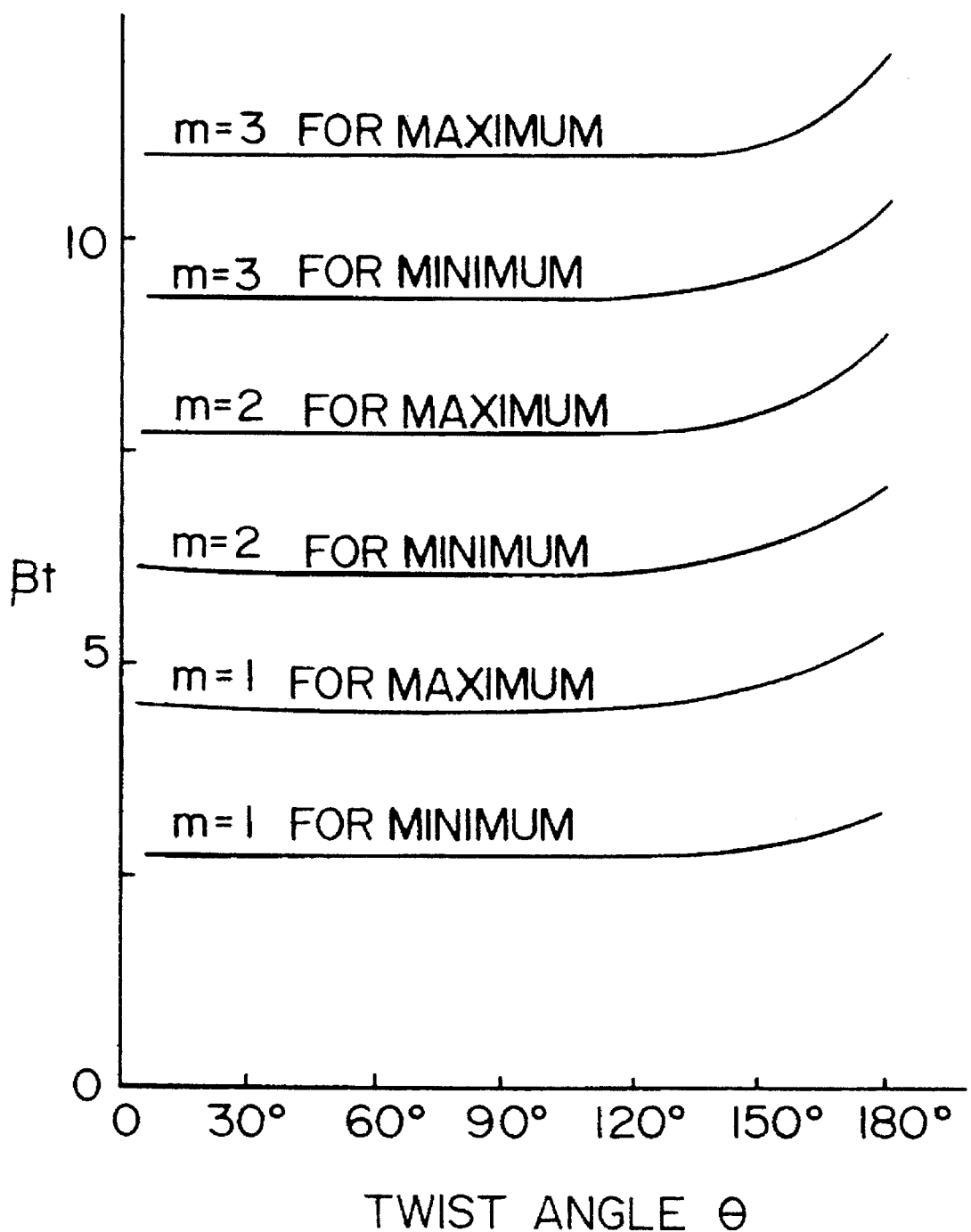
FIG. 4 is a graph showing a relationship between the twist angle $\theta$ and $\beta_t$ at which the transmission T has an extreme.

Next a second embodiment of the present invention is described. In equation (4), the value $\beta$ (denoted as $\beta_t$) at which the transmission T has an extreme is a function of the twist angle $\theta$ of the liquid crystal cell. The relation between $\beta_t$ and $\theta$ is plotted in FIG. 4. It is noted that $\beta_t$ is almost constant for $\theta$ around 90°. In fact the variation of $\beta_t$ with $\theta$ between 0° and 120° is within 0.9% of the value of $\beta_t$ at $\theta=90°$ (denoted as $\beta_{t90}$). Therefore, allowing an error of 0.9%, one can use $\beta_{t90}$ instead of $\beta_t$ for $\theta$ between 0° and 120°. For the twist angle $\theta$ of 90° the equation (4) becomes $$T=\sin^2\gamma.$$

Therefore, $\beta_t$ at which T has m-th minimum is given by $\beta_t=\pi\sqrt{(m^2-\frac{1}{4})}$, where m=1, 2, 3, . . . , and $\beta_t$ at which T has m-th maximum is given by $\beta_t=\pi\sqrt{(m^2+m)}$, where m=1, 2, 3, . . .

Using $\beta=\pi\Delta nd/\lambda$ and the observed wavelengths $\lambda$, $\Delta nd=\lambda\sqrt{(m^2-\frac{1}{4})}$ for the minimal transmission and $\Delta nd=\lambda\sqrt{(m^2+\frac{1}{4})}+ee$ for the maximal transmission.

Figure 6:
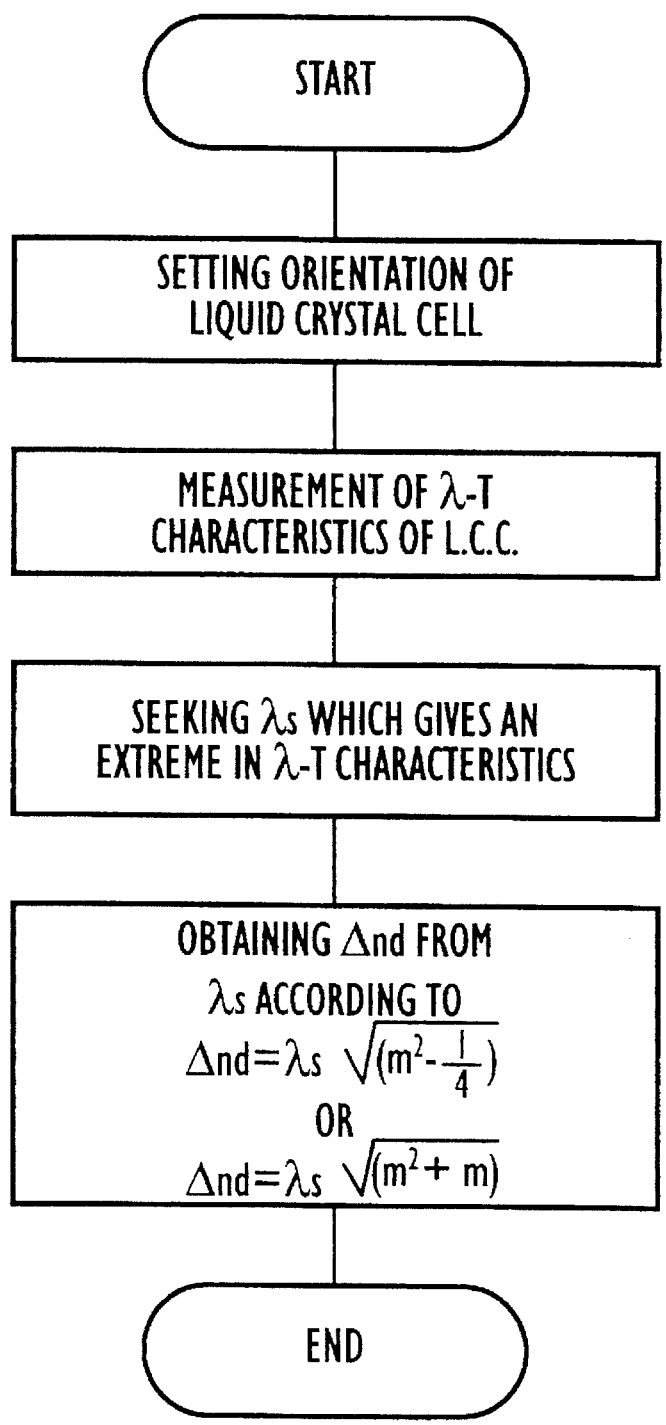
FIG. 6 is a flow chart for showing a second preferred embodiment of the measuring method of $\Delta nd$ according to the present invention.

Generally, a method of measuring optical characteristics of a liquid crystal cell according to the second embodiment is summarized in a flow chart shown in FIG. 6. That is, a linearly polarized light beam is incident on a liquid crystal cell, and the liquid crystal cell is rotated in the plane normal to the optical axis thereof so that the transmission for a component of the emerging light beam from the liquid crystal cell having a polarization parallel to that of the incident beam has a maximal value. In this configuration, the transmission is given by equation (4) and is independent of the direction of rubbing of the liquid crystal. In the same configuration, the transmission is measured next in scanning the wavelength of the incident light beam and one measures the wavelength $\lambda_s$ at which the transmission has an extreme.

For the case of the extreme being a minimum, one obtains the $\Delta nd$ of the liquid crystal from the observed wavelength $\lambda_s$ and $\Delta nd=\lambda_s\sqrt{(m^2-\frac{1}{4})}$. For the case of the extreme being a maximum, one obtains the $\Delta nd$ of the liquid crystal using the observed wavelength $\lambda_s$ and $\Delta nd=\lambda_s\sqrt{(m^2+m)}$.

Figure 7:
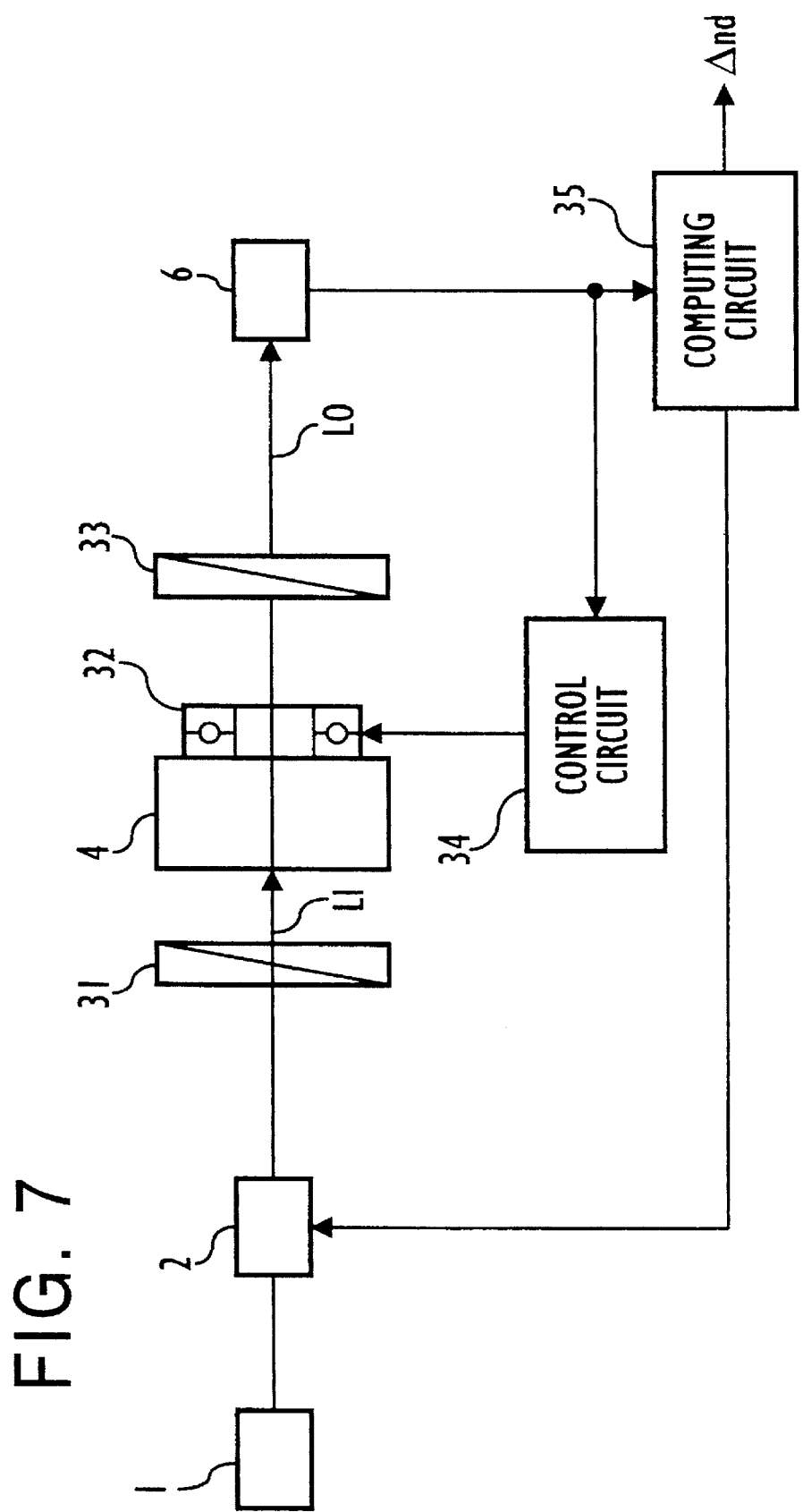
FIG. 7 is a block diagram of a measuring apparatus of $\Delta nd$ of a liquid crystal cell according to the present invention.

Next an embodiment of optical equipment for measuring optical characteristics of a liquid crystal cell of the present invention is described with reference to FIG. 7. Numeral reference 1 in the figure is a light source, 2 means for separating wavelengths, 4 a liquid crystal cell, and 6 a photo detector. Reference numeral 31 is a polarizer, 32 a rotation means for rotating the liquid crystal cell in the plane normal to the optical axis of the optical equipment which may be a rotary encoder, 33 another polarizer having the polarization axis parallel to that of polarizer 31, 34 a control circuit for setting the direction of liquid crystal cell 4 using rotation means 32 so that the transmission has a maximum, and 35 a computing circuit which drives means for separating wavelengths 2, measures extremes of the transmission, and computes the $\Delta nd$.

The output of photo detector 6 is proportional to the transmission given by equation (3), where $\lambda$ is the wavelength of light beam LI emerging from wavelength separating means 2. After rotating liquid crystal cell 4 with direction setting means 34 to make the transmission to have a maximum, the output of photo detector 6 is proportional to the transmission given by equation (4). Therefore, by scanning the wavelength of incident light beam LI on liquid crystal cell 4 by wavelength separating means 2 and by measuring extremes of the output of the photo detector 6, one can obtain the $\Delta nd$ of liquid crystal cell 4 using the observed wavelength and $\Delta nd=\lambda\sqrt{(m^2-\frac{1}{4})}$ for the minimal output, or $\Delta nd=\lambda\sqrt{(m^2+m)}$ for the maximal output.

In summary, according to the optical equipment of the present invention, the $\Delta nd$ of the liquid crystal is obtained by placing the liquid crystal cell to measure between two polarizers of which polarization axes are set parallel to each other, by rotating the liquid crystal cell so that the transmission has a maximum, and by scanning wavelength with wavelength separating means 2 to measure the wavelength at which the output of the photo detector has an extreme. The obtained $\Delta nd$ is independent of the twist angle and the direction of rubbing of the liquid crystal cell.

In this embodiment the polarization axes of the polarizers are fixed and the liquid crystal cell is rotated. The same effect is obtained, however, by rotating both the polarizers keeping the liquid crystal cell fixed instead.

According to the present invention the $\Delta nd$ is measured regardless of the value of the twist angle and the direction of rubbing of the liquid crystal cell.

Although present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A method for measuring retardation $\Delta nd$ of a liquid crystal cell having a known twist angle comprising steps:

inputting a linearly polarized light beam, having a wavelength, to said liquid crystal cell;

rotating said liquid crystal cell in a plane normal to an optical axis of a measuring optical system so that the transmission through said liquid crystal cell for a component of an emerging light beam having a polarization parallel to that of said linearly polarized light beam becomes maximal;

scanning the wavelength of said linearly polarized light beam to detect at least one wavelength at which the transmission of said component of said emerging light beam has a maximum or minimum value; and calculating retardation $\Delta nd$ of said liquid crystal cell based upon said known twist angle and at least one wavelength detected.

2. The method as claimed in claim 1 wherein retardation $\Delta nd$ is obtained from an equation $$\Delta nd = \beta_t \lambda_s / \pi$$

wherein $\beta_t$ and $\lambda_s$ are values of $\beta$ and wavelength $\lambda$ at which the transmission T given by the following equation has an extreme, $$T = [\cos \gamma \cos \theta + (\theta/\gamma) \sin \gamma \sin \theta]^2 + [(\beta/\gamma) \sin \gamma \cos (\theta + 2\phi)]^2$$

in which $\theta$ is the twist angle, $\gamma = \sqrt{\beta^2 + \theta^2}$ $\beta = \pi \Delta nd/\lambda$ and $\phi$ is a rotation angle of said liquid crystal cell.

3. A method for measuring retardation $\Delta nd$ of a liquid crystal cell comprising steps:

inputting a linearly polarized light beam having a wavelength to said liquid crystal cell, rotating said liquid crystal cell in a plane normal to an optical axis of a measuring optical system so that the transmission through said liquid crystal cell for a component of an emerging light beam having a polarization parallel to that of said linearly polarized light beam becomes maximal, scanning the wavelength of said linearly polarized light beam to detect wavelengths $\lambda_s$ at each of which the transmission of said component of said emerging light beam has an m-th extreme (wherein m is a positive integer representing the order of each extreme), and calculating retardation $\Delta nd$ in accordance with a) $\Delta nd = \lambda_s \sqrt{m^2 - 1/4}$ for the case in that m-th extreme is minimal, and $\Delta nd = \lambda_s \sqrt{m^2 + m}$ for the case in that m-th extreme is maximal.

4. The method as claimed in claim 3 wherein said liquid crystal cell is rotated by an angle at which the transmission for said component of said emerging light beam become maximal in which the transmission T is given by an equation $$T = [\cos \gamma \cos \theta + (\theta/\gamma) \sin \gamma \sin \theta]^2 + [(\beta/\gamma) \sin \gamma \cos (\theta + 2\phi)]^2$$

wherein $\theta$ is a twist angle of said liquid crystal cell, $\gamma = \sqrt{\beta^2 + \theta^2}$, $\beta = \pi \Delta nd/\lambda$ and $\phi$ is a rotation angle of said liquid crystal cell.

5. A device for measuring optical characteristics of a liquid crystal comprising:

a light source which emits a light beam having a variety of wavelengths;

a wavelength separation means for separating a beam having a specific wavelength from said light beam emitted from said light source in a variable manner;

a first polarizer on which said beam having said specific wavelength is incident, a liquid crystal cell on which an emerging light beam from said first polarizer is incident, a rotation means for rotating said liquid crystal cell in a plane normal to an optical of said device, a second polarizer, having a polarization axis parallel to a polarization axis of said first polarizer on which an emerging beam from said liquid crystal cell is incident, a set means for setting a rotation angle of said liquid crystal cell so that an output of said photo detector becomes maximal, a scan means for varying said specific wavelength, a detection means for detecting information regarding at least one extreme of the transmission of an emerging beam from said second polarizer when said specific wavelength is varied, and a calculation means for calculating retardation $\Delta nd$ of said liquid crystal cell based on said information and a value of said specific wavelength at which the transmission has an extreme.

6. The device as claimed in claim 5 in which said set means determines said rotation angle of said liquid crystal cell based on an equation:

$$T = [\cos \gamma \cos \theta + (\theta/\gamma) \sin \gamma \sin \theta]^2 + [(\beta/\gamma) \sin \gamma \cos (\theta + 2\phi)]^2$$

wherein

T is the transmission of an emerging beam from said second polarizer, $\theta$ is the twist angle, $\gamma = \sqrt{\beta^2 + \theta^2}$, $\beta = \pi \Delta nd/\lambda$ and $\phi$ is said rotation angle of said liquid crystal cell.

7. The device as claimed in claim 5 in which said information is a wavelength at which the transmission has an extreme and an order of said extreme.

8. The device as claimed in claim 7 in which said extreme is minimal and the retardation of said liquid crystal cell is obtained from an equation:

$$\Delta nd = \lambda_s \sqrt{m^2 - 1/4}$$

wherein $\lambda_s$ is a wavelength at which the transmission becomes minimal and m is an order of said extreme in which said extreme occurs.

9. The device as claimed in claim 7 in which said extreme is maximal and the retardation of said liquid crystal cell is obtained from an equation:

$$\Delta nd = \lambda_s \sqrt{m^2 + m}$$

wherein $\lambda_s$ is a wavelength at which the transmission becomes minimal and m is an order of said extreme in which said extreme occurs.

10. A method for manufacturing liquid crystal cells including an inspection process of retardation $\Delta nd$ of respective liquid crystal cells having a known twist angle which comprises steps:

inputting a linearly polarized light beam having a wavelength to said liquid crystal cell, rotating said liquid crystal cell in a plane normal to an optical axis of a measuring optical system so that the transmission through said liquid crystal cell for a component of an emerging light beam having a polarization parallel to that of said linearly polarized light beam becomes maximal, scanning the wavelength of said linearly polarized light beam to detect at least one wavelength at which the transmission of said component of said emerging light beam has an extreme, and calculating retardation $\Delta nd$ of said liquid crystal cell based upon said known twist angle and at least one wavelength detected.

11. A method for manufacturing liquid crystal cells including an inspection process of retardation $\Delta nd$ of respective liquid crystal cells which comprises steps:

inputting a linearly polarized light beam having a wavelength to said liquid crystal cell, rotating said liquid crystal cell in a plane normal to an optical axis of a measuring optical system so that the transmission through said liquid crystal cell for a component of an emerging light beam having a polarization parallel to that of said linearly polarized light beam becomes maximal, scanning the wavelength of said linearly polarized light beam to detect wavelengths $\lambda_s$ at each of which the transmission of said component of said emerging light beam has an m-th extreme (wherein m is a positive integier representing the order of each extreme), and calculating retardation $\Delta nd$ in accordance with a) $\Delta nd = \lambda_s \sqrt{m^2 - \frac{1}{2}}$ for the case in that m-th extreme is minimal, and b) $\Delta nd = \lambda_s \sqrt{m^2 + m}$ for the case in that m-th extreme is maximal.

* * * * *